(12) United States Patent
Bellaton et al.

(10) Patent No.: US 9,970,851 B2
(45) Date of Patent: May 15, 2018

(54) MEASURING HEAD FOR NANOINDENTATION INSTRUMENT AND MEASURING METHOD

(71) Applicant: ANTON PAAR TRITEC SA, Peseux (CH)

(72) Inventors: Bertrand Bellaton, Neuchâtel (CH); Richard Consiglio, Neuchâtel (CH); Jacques Woirgard, La Grimaudière (FR)

(73) Assignee: ANTON PAAR TRITEC SA, Peseux (CH)

( * ) Notice: Subject to any disclaimer, the term of this patent is extended or adjusted under 35 U.S.C. 154(b) by 137 days.

(21) Appl. No.: 14/898,435

(22) PCT Filed: Jun. 16, 2014

(86) PCT No.: PCT/EP2014/062606
§ 371 (c)(1),
(2) Date: Dec. 14, 2015

(87) PCT Pub. No.: WO2014/202551
PCT Pub. Date: Dec. 24, 2014

(65) Prior Publication Data
US 2016/0153881 A1    Jun. 2, 2016

(30) Foreign Application Priority Data

Jun. 17, 2013  (EP) .................................... 13172349

(51) Int. Cl.
*G01N 3/42*  (2006.01)
*G01Q 60/36*  (2010.01)
*G01Q 60/24*  (2010.01)

(52) U.S. Cl.
CPC ............... *G01N 3/42* (2013.01); *G01Q 60/24* (2013.01); *G01Q 60/366* (2013.01);
(Continued)

(58) Field of Classification Search
CPC ......... G01N 3/42; G01Q 60/24; G01Q 60/366
See application file for complete search history.

(56) References Cited

U.S. PATENT DOCUMENTS

| 7,685,868 | B2 | 3/2010 | Woirgard |
| 2008/0028840 | A1 | 2/2008 | Smith |
| 2009/0013770 | A1* | 1/2009 | Proksch ................. G01Q 60/32 73/105 |

FOREIGN PATENT DOCUMENTS

| EP | 1 482 297 A1 | 12/2004 |
| JP | 2004-271318 A | 9/2004 |

OTHER PUBLICATIONS

International Search Report dated Aug. 26, 2014, issued in corresponding International Application No. PCT/EP2014/062606, filed Jun. 16, 2014, 3 pages.

(Continued)

*Primary Examiner* — Hezron E Williams
*Assistant Examiner* — David Z Huang
(74) *Attorney, Agent, or Firm* — Christensen O'Connor Johnson Kindness PLLC

(57) ABSTRACT

A measuring head for a nano-indentation instrument, said nano-indentation instrument comprising a positioning system arranged to position a sample relative to the measuring head, the measuring head comprising:
a measuring subsystem attached to a frame adapted to be connected to the nano-indentation instrument, the measuring subsystem comprising a first actuator and an indenter adapted to indent a surface of said sample under application of a force applied by the first actuator on the indenter, the measuring subsystem further comprising a force sensing system adapted to detect said force applied by the first actuator;
a reference subsystem attached to said frame, the reference subsystem comprising a second actuator, a refer-
(Continued)

ence structure in operative connection with the second actuator, and a separation detector adapted to determine a predetermined separation of the reference structure and said surface of said sample.

19 Claims, 1 Drawing Sheet

(52) U.S. Cl.
CPC ............... *G01N 2203/0078* (2013.01); *G01N 2203/0286* (2013.01); *G01N 2203/0641* (2013.01)

(56) References Cited

OTHER PUBLICATIONS

International Preliminary Report on Patentability dated Aug. 28, 2015, issued in corresponding International Application No. PCT/EP2014/062606, filed Jun. 16, 2014, 9 pages.

\* cited by examiner

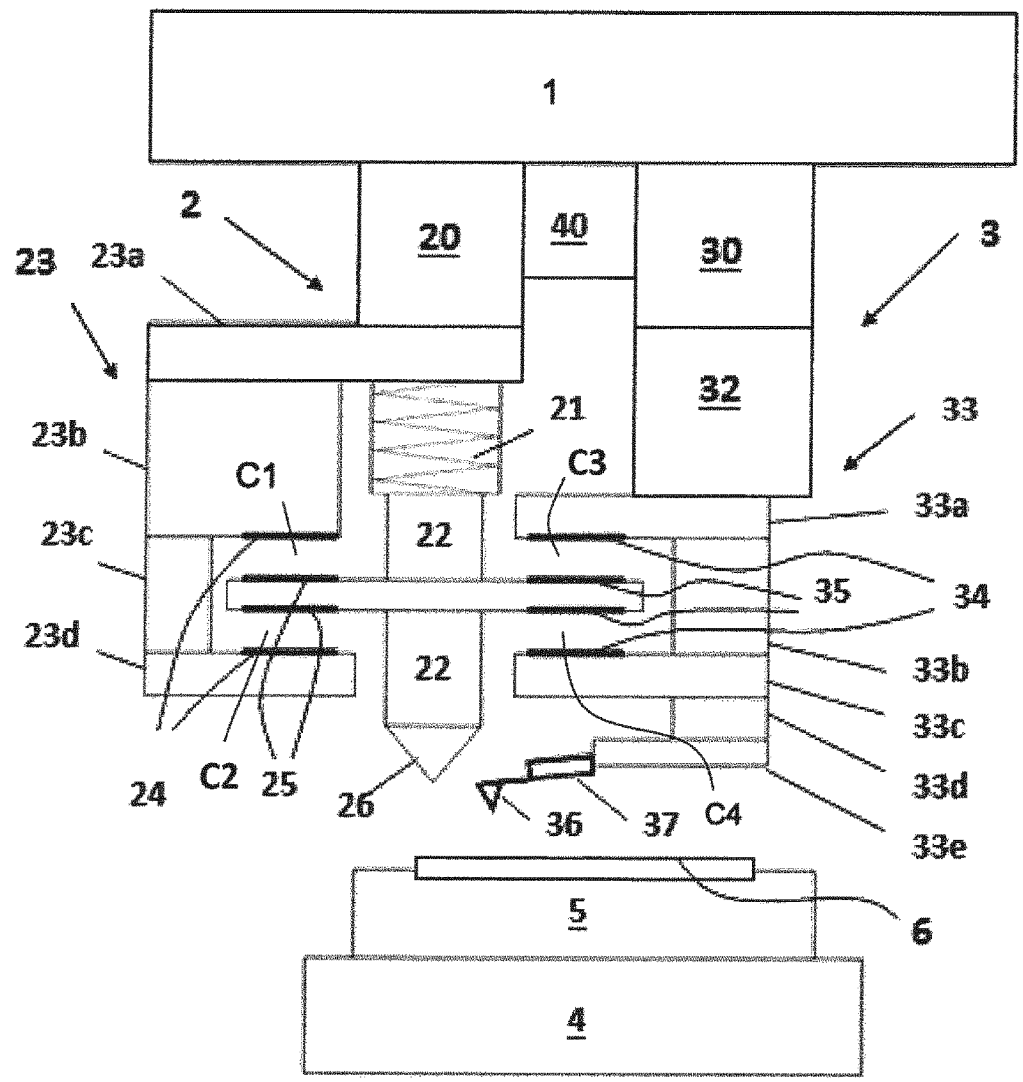

MEASURING HEAD FOR NANOINDENTATION INSTRUMENT AND MEASURING METHOD

TECHNICAL FIELD

The present invention relates to nano-indentation measuring instruments and more particularly to a measuring head for such an instrument comprising an active positioning referencing of the surface of the sample, as well as to a method of measuring a depth of penetration of an indenter into a sample using said measuring head.

STATE OF THE ART

Depth-sensing Indentation ("DSI") methods are frequently used for determining certain mechanical properties of materials, such as for example the elastic modulus and hardness. These methods consist of applying a force on a sample via an indenter having a precise and known shape, in order to investigate and to measure the values of the load applied on the sample on one hand and the penetration depth of the indenter tip on the other hand.

These instruments become more and more sophisticated as the measured forces to be measured become smaller and smaller. Also, the surfaces over which the measurements have to be performed are becoming smaller and smaller and the range of materials to be tested is widening. For example, there is a growing need to test layers with a thickness less than several nanometers (nm) and of which the width can be smaller than a few μm. The involved forces may be smaller than a few micro-Newtons (μN), the displacement of the indenter to be measured may be of the order of one nanometer (nm) or smaller, and the measurement surfaces of the samples to be tested can be smaller than 20×20 μm.

U.S. Pat. No. 7,685,868 discloses a nano-indentation measuring instrument, the measuring head of which includes an indenter axis and a reference axis, that allows measurement of the elastic modulus and of the hardness at a nanoscale. The measuring head described in U.S. Pat. No. 7,685,868 is based on a measuring subsystem and a reference subsystem that each comprise their own actuation and displacement means of their respective axes, as well as a force feedback system to control the force applied to these axes. Furthermore, using an active reference axis, it is possible, by monitoring the force applied to the sample by the reference axis by using piezo actuators, to eliminate parasitic movements of the surface of the sample relative to the indenter, which can occur due to changing temperatures or deformations of the frame to which the sample is connected.

The measuring head described in U.S. Pat. No. 7,685,868 presents at least the following performance limitations:

The described measuring head uses a relatively complex system comprising two axes, one being an indenter axis and one being a reference axis. Both axes have a relatively large lateral dimension which imposes a relatively large separation between the extremities of these two axes. The relatively large separation between the reference tip and the indenter limits the precision of the measurement, because a large separation leads to measurement errors that may be induced by the flexure of the system, the vibration of the sample, or temperature effects.

Furthermore, the accuracy of placement of the indenter is limited to several microns or even several tens of microns by the fact that a separate topographical scanner placed to the side of the measurement head is required to identify the areas of interest for indentation. A separate topographical scanner implies a relatively large displacement of the sample from the scanner to the indenter, limiting the precision of targeting the indentation position.

Another example of a prior-art indenter is disclosed in document US2008/028840. This document discloses the use of an atomic force microscope as part of a reference sensor for indentation measurement. Furthermore, document EP1482297 discloses a scanning probe microscope.

SUMMARY OF THE INVENTION

The object of this invention is therefore to overcome at least partially the limitations of the measuring heed described in the prior art. This object is achieved by a measurement head for a nano-indentation instrument, which latter comprises a positioning system arranged to position a sample relative to the measuring head.

The measuring head comprises a measuring subsystem that is attached to a frame adapted to be connected to the nano-indentation instrument, and comprising a first actuator and an indenter adapted to indent a surface of said sample under application of a force applied by the first actuator on the indenter.

The measuring subsystem further comprises:
a force sensing system adapted to detect said force applied by the first actuator;
a reference subsystem attached to said frame, the reference subsystem comprising a second actuator, a reference structure in operative connection with the second actuator, and a separation detector adapted to determine a predetermined separation of the reference structure and said surface of said sample.

According to the invention, the measuring head comprises a relative position sensing system that is adapted to determine the position of the indenter relative to the reference structure. The measuring head further comprises means for determining a depth of penetration of the indenter in the sample, the measurement of the penetration depth being based, at least partially, on an output of the relative position sensing system. The separation detector of the measurement head comprises a topographic tip protruding from the reference structure and is arranged to contact said surface of said sample. A topographic tip is a measurement tip that can be used for measuring the surface topography of a sample, examples of which include but are not limited to micromechanical tips such as an atomic force microscope (AFM) tip (whether vibrating or not), and non contacting tips such a near-field scanning optical microscope (NSOM) tip, and so on.

Alternatively, micro-optic tips utilising optical beams such as laser beams can be used, or combined micromechanical and micro-optic tips, such as the combination of an AFM tip with a laser arranged to measure displacement of the AFM tip.

Thereby, the penetration depth is measured based on the relative position of the indenter and the reference structure, which can be positioned a known distance from the surface of the sample by means of the topographic tip, rather than relying on the more complicated arrangement of U.S. Pat. No. 7,685,868. In consequence, the measuring head is simplified, and the topographic tip can be placed significantly closer to the indenter than is possible with the reference tip of the prior art. Furthermore, due to the use of the topographic tip, a good quality scan of the topography of the surface of the sample is possible directly using the topographic tip arranged on the measuring head itself, thereby eliminating the necessity to use a separate scanning system positioned to the side of the measurement head, end/or eliminating the requirement to perform a poor quality topographic scan e.g. by using the indenter itself.

Essentially, the topographical scanning functionality is thereby integrated with the indenter. In consequence, much more accurate targeting of the position of the indenter, down to the order of a few manometers, is possible due to the significantly reduced displacement of the sample between scanning and indentation.

In an embodiment, the topographic tip of the measuring head is arranged on a resilient blade or cantilever that is operatively connected with a contact detector adapted to detect a contact of the topographic tip with said sample. As a result, very precise determination of the contact between the topographic tip and the substrate is possible due to the fact that the topographic tip can follow with very high speed and very high precision the movement of the surface of the sample, for example when the measuring head undergoes parasitic vibrations. This can be used for instance to permit extremely precise control of the position of the indenter with respect to the surface of the sample by means of very precise servocontrol.

In a preferred embodiment of the invention, the topographic tip of the measurement head is an atomic force microscope tip. Preferably, the atomic force microscope tip is arranged to be vibrated at a predetermined frequency, and the said contact detecting device is adapted to detect a change in vibration frequency and/or a change in vibration amplitude of the atomic force microscope tip away from the predetermined frequency and/or amplitude respectively when the atomic force microscope tip enters into contact with the surface of the sample. Contact between the atomic force microscope tip and the sample can thus be precisely determined, thereby precisely determining the position of the reference structure with respect to the surface of the sample.

According to an embodiment of the invention, the relative position sensing system preferably comprises a capacitive sensor, the capacitive sensor being further preferably arranged in a differential configuration, which results in a simple and accurate position sensing system.

The measurement head further comprises a servo-control circuit that is connected to said first actuator, allowing to control the force applied by the indenter on the sample. Said first actuator and second actuator of the measurement head preferably each comprise a piezoelectric actuator. Thus the separation of the reference structure from the surface of the sample can be kept constant irrespective of e.g. changes in temperature or flexure of some elements or portions of the measurement head.

According to an embodiment of the invention, the measuring head comprises also at least one optical vision system arranged on the measuring head, intended to record an image of the contact area of the atomic force microscope tip and/or of the contact area of the indenter and/or of the indented area. Thus, the operator can observe more easily the targeted portion of the surface to be indented or/and the indented areas of the sample.

The object of the invention is also achieved by a method of measuring a depth of penetration of an indenter into a sample. This method comprises providing a nano-indentation instrument comprising a measuring head as described above. A sample is positioned under the measuring head, and the reference structure is then positioned such that the topographic tip comes into contact with the sample. Subsequently, the indenter is put into contact with the sample, and a predetermined force is applied to the indenter for a predetermined period of time. At expiry of said predetermined period of time, the relative position between the indenter and the reference structure is determined.

The depth of penetration of the indenter into the sample is then determined, based at least partially on said determination of the relative position of the indenter and the reference structure.

Thereby, the penetration depth is measured based directly on the relative position of the indenter and the reference structure, which can be positioned a known distance from the surface of the sample by means of the topographic tip, rather than relying on the more complicated arrangement of U.S. Pat. No. 7,685,868. In consequence, greater measurement accuracy is possible.

In an embodiment, prior to the contact of the indenter with the sample for making the indentation, the targeted area to be indented may be scanned in order to determine precisely the position of the area to be indented. Thereby, a good quality scan of the topography of the surface of the sample is possible directly using the topographic tip of the measuring head itself, thereby eliminating the necessity to use a separate scanning system positioned to the side of the measurement head, and/or eliminating the requirement to perform a poor quality topographic scan e.g. by using the indenter itself. Since the topographical scanning functionality is integrated with the indenter, this topographical scanning can be formed in situ, and in consequence much more accurate targeting of the position of the indenter, down to the order of a few manometers, is possible due to the significantly reduced displacement of the sample between scanning and indentation.

In an embodiment of the method according to invention, the relative position of the indenter and the reference structure is determined when the indenter is brought into contact with the sample, the depth of penetration of the indenter into the sample being based at least partially on the determination of the relative position of the indenter and the reference structure when the indenter is brought into contact with the sample, and the determination of the relative position of the indenter with the reference structure at the expiry of said predetermined period of time. In consequence, even greater accuracy of measurement can be attained.

In an embodiment of the method, the topographic tip is positioned above the indentation caused by the indenter and the depth of that indentation is determined by lowering the topographic tip until the topographic tip contacts the inner surface of the indentation. Thus, verification of the measured indentation depth can be carried out, enhancing measurement reliability and precision.

In a further embodiment of the method, a plurality of indentations are formed, then the topographic tip is scanned over said plurality of indentations, and an image is produced of the depth profile of said plurality of indentations. The scanning by the topographic tip provides information on the profiles end depths of a part of the indentations of the surface and allows the production of an image of the depth profile of the indented area in which the plurality of indentations are situated.

BRIEF DESCRIPTION OF THE DRAWINGS

The above described objects and advantages of the present invention will become more readily apparent to those ordinarily skilled in the art after reviewing the following detailed descriptions and accompanying drawing, in which:

FIG. 1 shows an exemplary embodiment according to the invention.

DETAILED DESCRIPTION OF PREFERRED EMBODIMENTS

The following detailed description illustrates the principles of the invention. It will thus be appreciated that those skilled in the art will be able to devise various arrangements that, although not explicitly described or shown herein, embody the outlined principles of the invention and are included in the scope of the invention, as defined in the claims.

For reasons of clarity in the detailed explanations the following terms are defined:
"above" is to be interpreted as meaning towards the actuators of the measuring head;
"downward" and "beneath" are to be interpreted meaning towards the sample to be measured;

FIG. 1 illustrates a measuring head according to the invention, which comprises a frame 1 and two subsystems: a measuring subsystem 2 comprising an indenter 26 associated with a first actuator 20, and a reference subsystem 3 comprising a topographic tip 36 associated with a second actuator 30, the topographic tip 36 constituting at least part of a separation detector for determining a predetermined separation between the reference structure 33 (see below) and the surface of the sample. Said actuators 20, 30 are preferably of the piezoelectric type.

Said measuring subsystem 2 comprises also an indenter rod 22 on which said indenter 26 is arranged, a spring system 21 comprising at least one resilient element arranged on said indenter rod 22, and a body 23 linking the spring system 21 and the first actuator 20, and comprising a downwards-extending extension 23b, 23c, 23d that will be explained further in detail below. The said body 23 may be a single body or may be comprised of several portions 23 a-e, as illustrated in FIG. 1.

The surface material of the indenter 26 is preferably diamond, although other materials can be used, for example sapphire, or other less hard materials, such as hard steel, particularly in the case that softer samples are to be measured. If the measurement head is intended only to measure soft materials, the indenter rod 22 and the indenter 26 can be made in a single material, for example hard steel, with the indenter 26 shaped appropriately. It will be obvious for the skilled person that the indenter 26 may be arranged so that it can be easily replaced by another indenter 26. This could be advantageous for instance when materials of very different properties have to be measured and it becomes appropriate to change the type or/and shape of indenter 26.

Said indenter rod 22 comprises a first pair of electrodes 25 and a second pair of electrodes 35 that are arranged substantially perpendicular to the axis of the indenter rod 22. The first pair of electrodes 25 extends towards the body 23, and the second pair of electrodes 35 extends towards the reference structure 33.

Said body 23 comprises two electrodes 24 each facing a respective electrode of said first pair of electrodes 25, and arranged parallel thereto, so as to form a pair of capacitors. The capacitors C1 and C2 thus formed are arranged in a differential mode so as permit measurement of a displacement of the indenter rod 22 relative to said body 23, and form, together with the spring system 21, an applied force sensor, in the manner described in U.S. Pat. No. 7,685,868. Additionally, a control circuit is provided for the control of the actuator of the indenter rod 22, similar to the one used for the measurement axis described in U.S. Pat. No. 7,685,868.

The reference subsystem 3 comprises a cantilever 37 on which the topographic tip 36 is arranged, a holder 33d on which the cantilever 37 is arranged, and a reference structure 33 on which said holder is arranged. Said reference structure 33 is connected to said actuator 30 and comprises two electrodes 34 each facing a respective electrode of said second pair of electrodes 35 on the indenter rod 22, and arranged parallel thereto, so as to form a further pair of capacitors C3, C4. The further two capacitors C3 and C4 thus formed are arranged in a differential mode so that the displacement of the indenter rod can be measured relative to said reference structure 33, and thus also the displacement of the indenter 26 relative to the surface of the substrate, since the position of the reference structure 33 with respect to the substrate surface is known. As such, the further two capacitors C3 and C4 constitute a relative position sensing system.

In a typical arrangement, both electrodes of the second pair of electrodes 35 of said reference structure 33 may be arranged on transverse components 33a, 33c of said reference structure 33, as shown in FIG. 1, of which a first transverse component 33a is arranged parallel to and above a transverse component 27 of the indenter rod, and a second transverse component 33c arranged parallel and beneath the transverse component 27 of the indenter rod. In this arrangement, the transverse components 33a, 33c of the reference structure 33 are separated by a distance arranged such that said transverse component 27 of the indenter is arranged in between said transverse components 33a and 33c of said reference structure 33. The reference structure 33 may be constructed so that said holder 33d is an integral part of the reference structure 33.

It should be noted that the topographic tip 36 should ideally be positioned as closely as possible to the indenter 26.

The topographic tip 38 can be of a type intended to contact the surface of the sample, or it can be of a non contact type. Any convenient micromechanical microstructure can be used for a topographic tip 36 intended to be positioned 16 to the surface by contact. If the topographic tip has to be positioned to the surface without contact, an optical microstructure can be used, for example a fiber optic tip or any typical optical tip used in for example a near-field scanning optical microscope (NSOM), such as disclosed in http://www.nanoprobes.aist-nt.com, herein incorporated by reference in its entirely.

As the invention is practiced today, the topographic tip 36 is an atomic force microscope (AFM) tip. The dimension of the topographic tip 36 is typically smaller than 100 μm, preferably smaller than 30 μm. The radius of the extremity of said topographic tip 36 is in the scale of a few nm. The material of said topographic tip can be any hard material, preferably silicon, more preferably quartz. Different arrangements of said cantilever 37 are possible and are well known to the person skilled in the art, such as those disclosed in http://www.nanoandmore.com/afm-cantilevers.php, herein incorporated by reference in its entirely.

It is s noted that the reference structure 33 may comprise several portions 33a-33d, as illustrated in FIG. 1. In one possible arrangement, an intermediate structure 32 could be arranged between the actuator 30 and the reference structure 33. In another arrangement, said cantilever 37 can be arranged directly on said reference structure 33 without said holder 33d.

The measurement instrument further comprises, arranged under the measurement head, a sample holder 8 arranged on top of a sample positioning device comprising at least an x-y scanning system 5, said x-y scanning system being arranged on top of a vertical translator 4. Said x-y scanning system 5 may be a nano-positioning table and may further comprise a rotation axis allowing to rotate the sample around an axis perpendicular to its surface. In another variant, the rotation axis may be provided by the vertical translator 4. Said vertical translator 4 and said x-y scanning system 5 are well known to the skilled person and need not be further explained. The sample positioning device is connected to the frame of the measuring instrument so that the sample can be brought close to the topographic tip 36.

The body 23, the spring system 21, the reference structure 33 and the frame 1 of the measuring head should ideally have a mass and a thermal expansion coefficient which is as low as possible. The components of the measurement subsystem 2 and reference subsystem 3 may preferably be made in the same materials as mentioned in U.S. Pat. No. 7,685,868. The configuration of the force feedback system of the indenter subsystem 2 utilizing capacitors C1, C2 may be similar to that described in U.S. Pat. No. 7,685,868. The electrode materials may also be chosen similar to those described in U.S. Pat. No. 7,685,868. The spring system 21 can be provided with a mechanism such that the resilient component of the spring system 21, such as a spring, may be exchanged easily in order to be able to work with a different springs each having a different spring constant, so that different indentation depths of the surface of the sample can be measured.

The shape of the measuring head as illustrated in the FIG. 1 is not to be construed as limiting: different mechanical and geometrical variants of the invented measuring head are of course possible. The present invention further includes the possibility to arrange a translation mechanism 40 so that the reference subsystem 3 can be displaced relative to the measurement subsystem 2, for instance in a variant of the measurement head wherein the topographic tip 36 has to be removed or to allow access to the reference area with another measurement instrument or to allow to remove and replace easily the topographic tip and/or the cantilever 37. Advantageously, an optical vision system may be arranged on the measurement head, so as to permit visualization of the area to be measured, and/or to visualize the indented area and/or to visualize at the same time the topographic tip 36 and the indenter tip 26, or to check for any contamination of the surface. Further, the optical vision system may deliver a 2D or 3D image that may be correlated to the indentation profile determined by the topographic tip 36.

A method of operation of the measurement head of the invention and in particular that of the sensors will now be explained in more detail.

A sample positioning system 4, 5, 6 comprises a holder 6 or a geometrical arrangement so that the sample is firmly attached to said sample positioning system and substantially perpendicular to the axis of the indenter rod 22. Prior to positioning the sample, the indenter is positioned by means of the actuator 20 of the measurement subsystem 2, so that it is situated further away from the surface of the sample than the topographic tip 36. The typical distance difference between the indenter 26 and the topographic tip 36 is 200 µm, preferably less than 50 µm. Subsequently, the sample positioning system brings the sample to a predetermined position close to the topographic tip 36, typically at a distance of several µm therefrom. If required, the sample may also be turned and positioned around an axis perpendicular to the surface of the sample, for example to align a rectangular shaped microdeposition layer with one of the x and y scan axes of the sample positioning system.

Prior to contact with the surface of the sample, the topographic tip 36 is, if necessary, put into a state that permits detection of contact between the topographic tip 36 and the sample, as will be explained further. The method of detection of contact depends on the type of the topographic tip 36, and may in its simplest form merely comprise detection of force and/or movement of the topographic tip or its supporting structure. A particularly advantageous method of detection of contact in the case that the topographic tip 36 is an atomic force microscope (AFM) tip 36 will be explained in detail in the following. The skilled person knows how to adapt the method for other types of tip. In the case of an AFM tip 36, the AFM tip is vibrated at a predetermined frequency and with a predetermined amplitude.

After a stable predetermined frequency and amplitude vibration is induced, the actuator 30 of the reference subsystem 3 moves the AFM tip 36 towards the surface of the sample until the AFM tip 36 is extremely close, typically 1 µm, to the surface of the sample. The approach speed between the sample and AFM tip 36 may then be reduced until contact with said AFM tip 36 is detected. Thus, the reference structure 33 is positioned at a predetermined, known, separation from the surface of the sample.

There are several ways to detect the contact of said topographic tip 36 with the surface of a sample. In a preferred method, said contact is detected by a change of the predetermined vibration frequency of said topographic tip 36. Upon contact, the vibration characteristics of the AFM tip 36 will be altered and a frequency shift will occur. The detection of a predetermined frequency shift is used as the signal of contact of said AFM tip 36 with the surface of the sample. At that precise event, the positioning reference AFM tip 36 may be kept into its position by the actuator 30 of the measurement subsystem 3, e.g. by means of a feedback loop in which a signal provided by the AFM tip 36 is used to control the actuator 30.

In another variant, a predetermined amplitude variation of the vibration of the topographic tip 36 can be applied to detect contact of the AFM tip 36 with the surface of the sample. In yet another variant both a frequency and an amplitude variation of the vibration of the topographic tip 36 can be used. It should be noted that the present invention is not limited to electrical signals delivered by the topographic tip 36 to detect the contact position and other methods may be used, for example optical methods such as optical interferometric methods or typical methods used in arrangements comprising a near-field scanning optical microscope. In a further variant of the invention, at least two topographic tips 36 could be arranged at the extremity of said reference structure 33, and their combined delivered signals could be used to improve the position reference accuracy.

When the topographic tip 36 has contacted the surface of the sample, the topographic tip 36 will be kept, during the entire indentation measurement cycle, in contact with the surface, e.g. by a feedback circuit that utilizes the change of the signal generated by the topographic tip 36 and that acts upon the actuator 30 of the reference subsystem 3. This assures that the position of the reference structure 33 relative to the surface of the sample is precisely known during the entire indentation measurement cycle.

Prior to indentation, the topographic tip 36 can be scanned over a predetermined area of the surface of the sample in order to determine a topographic image that represents the surface profile of that area and to identify the precise place where the indentation measurement has to be performed. As the topographic tip 36 is arranged very close to the indenter 26, the lateral displacement of the indenter to the very precise place to be indented is very small and equal to the distance separation between the topographic tip and the indenter.

Once the topographic tip 36 is put in contact with the targeted surface of the sample, the indentation measurement cycle may begin. The indenter 26 is first lowered close to the surface to be measured, typically at some μm. The speed of the actuator 20 is then reduced until the indenter 26 touches the surface of the sample to be measured. Contact of the indenter 26 with the surface of the sample can be detected e.g. by using the signals of the force feedback system and the information of the position of the indenter 26 relative to the topographic tip 36.

Conventionally, during the measurement cycle, a certain predetermined force may be applied during the indentation measurement. However, the applied predetermined force may also vary during the measurement, and/or the measurement subsystem 2 may deliver a variable force so that a certain predetermined depth of the indenter is achieved in the surface of the sample, while measuring the force applied by the indenter 26. It is also possible to perform an indentation at least two times at the same measurement location, or at different locations.

Furthermore, the topographic tip 36 may be brought above the indented position and lowered into the previously-produced indentation so as to determine the indentation profile and the indentation depth of said indentation. Repetitive indentations may be performed at different or contiguous places in a predetermined area and measurements of the indentation depths and/or profiles may be subsequently be performed in order to obtain a 2D or 3D image of the indented area.

The invention claimed is:

1. A measuring head for a nano-indentation instrument, said nano-indentation instrument comprising a positioning system arranged to position a sample relative to the measuring head, the measuring head comprising:
a measuring subsystem attached to a frame adapted to be connected to the nano-indentation instrument, the measuring subsystem comprising a first actuator and an indenter adapted to indent a surface of said sample under application of a force applied by the first actuator on the indenter, the measuring subsystem further comprising a force sensing system adapted to detect said force applied by the first actuator;
a reference subsystem attached to said frame, the reference subsystem comprising a second actuator, a reference structure in operative connection with the second actuator, and a separation detector adapted to determine a predetermined non-zero separation of the reference structure and said surface of said sample,
the measuring head further comprising:
a relative position sensing system adapted to determine a relative position of the indenter and the reference structure;
means for determining a depth of penetration of the indenter in a surface of the sample based at least partially on an output of the relative position sensing system;
wherein said separation detector comprises a topographic tip protruding from the reference structure and arranged to contact said surface of said sample,
wherein said relative position sensing system comprises two electrodes arranged on said indenter rod, and two electrodes arranged on said reference structure each arranged facing a respective electrode arranged on the indenter rod, said electrodes forming a pair of capacitors.

2. The measuring head according to claim 1, wherein the topographic tip is arranged on a cantilever, the resilient cantilever being operatively connected with a contact detector adapted to detect a contact of the topographic tip with said sample.

3. The measuring head according to claim 1, wherein said topographic tip is an atomic force microscope tip.

4. The measuring head according to claim 3, wherein the atomic force microscope tip is arranged to be vibrated at a predetermined frequency, and wherein said contact detecting device is adapted to detect a change in vibration frequency of the atomic force microscope tip away from said predetermined frequency when the atomic force microscope tip enters into contact with the surface of the sample.

5. The measuring head according to claim 3, wherein the atomic force microscope tip is arranged to be vibrated at a predetermined amplitude, and wherein said contact detecting device is adapted to detect a change in vibration amplitude of the atomic force microscope tip away from said predetermined amplitude when the atomic force microscope tip enters into contact with the surface of the sample.

6. The measuring head according to claim 3, wherein at least one optical vision system is arranged on the measuring head, and is arranged to record an image of a contact area of the atomic force microscope tip or a contact area of the indenter.

7. The measuring head according to claim 3, wherein at least one optical vision system is arranged on the measuring head, and is arranged to record an image of a contact area of the atomic force microscope tip and a contact area of the indenter.

8. The measuring head according to claim 1, wherein a servo-control circuit is connected to said first actuator in order to control the force applied by the indenter on the sample.

9. The measuring head according to claim 1, wherein said first actuator or second actuator comprises a piezoelectric actuator.

10. The measuring head according to claim 1, wherein said first actuator and second actuator each comprise a piezoelectric actuator.

11. The measuring head according to claim 1, wherein said electrodes arranged on said reference structure are arranged to be used exclusively for measuring the relative displacement between the indenter and the reference structure.

12. The measuring head according to claim 1, wherein said electrodes arranged on said reference structure and said electrodes arranged on the indenter rod are configured such that they are the only electrodes implicated in measuring the relative position of the indenter and the reference structure.

13. The measuring head according to claim 1, wherein said predetermined non-zero separation is constant.

14. The measuring head according to claim 1, wherein said separation detector and said relative position sensing system are distinct one from the other.

15. A method of measuring a depth of penetration of an indenter into a sample, the method comprising the following steps:
providing a nano-indentation instrument comprising a measuring head according to claim 1;

positioning a sample under the measuring head;

positioning the reference structure such that the topographic tip comes into contact with the sample;

bringing the indenter into contact with the sample;

applying a predetermined force to the indenter for a predetermined period of time;

at the expiry of said predetermined period of time, determining the relative position of the indenter and the reference structure;

determining the depth of penetration of the indenter into the sample at least partially based on said determination of the relative position of the indenter and the reference structure.

16. Method according to claim 15, wherein, before bringing the indenter into contact with the sample, a surface of the sample is scanned by using said topographic tip, and a topographic image is produced of the surface of the sample.

17. Method according to claim 15, further comprising determining the relative position of the indenter and the reference structure when the indenter is brought into contact with the sample, the depth of penetration of the indenter into the sample being based at least partially on the determination of the relative position of the indenter and the reference structure when the indenter is brought into contact with the sample, and the determination of the relative position of the indenter and the reference structure at the expiry of said predetermined period of time.

18. Method according to claim 15 wherein, after indentation by the indenter, the topographic tip is positioned above the indentation caused by the indenter and the depth of the indentation is determined by lowering the topographic tip until the topographic tip contacts a surface of the indentation.

19. Method according to claim 15 wherein a plurality of indentations are formed, subsequently the topographic tip is scanned over said plurality of indentations, and an image is produced of the depth profile of said plurality of indentations.

* * * * *